US011185652B2

United States Patent
Eifler

(10) Patent No.: US 11,185,652 B2
(45) Date of Patent: Nov. 30, 2021

(54) DEVICE CONSISTING OF AT LEAST TWO MATERIALS

(71) Applicant: Martin Eifler, Glueckstadt (DE)

(72) Inventor: Martin Eifler, Glueckstadt (DE)

(73) Assignee: Loewenstein Medical Technology S.A., Luxembourg (LU)

( * ) Notice: Subject to any disclaimer, the term of this patent is extended or adjusted under 35 U.S.C. 154(b) by 868 days.

(21) Appl. No.: 13/958,705

(22) Filed: Aug. 5, 2013

(65) Prior Publication Data

US 2013/0344293 A1 Dec. 26, 2013

Related U.S. Application Data

(63) Continuation of application No. 12/317,259, filed on Dec. 19, 2008, now Pat. No. 8,535,771.

(30) Foreign Application Priority Data

Dec. 20, 2007 (DE) .......................... 102007062445.1

(51) Int. Cl.
| | |
|---|---|
| *A61M 16/06* | (2006.01) |
| *B29C 45/16* | (2006.01) |
| *A61M 16/08* | (2006.01) |
| *A62B 18/02* | (2006.01) |
| *A62B 18/08* | (2006.01) |

(Continued)

(52) U.S. Cl.
CPC ........ *A61M 16/06* (2013.01); *A61M 16/0616* (2014.02); *A61M 16/0622* (2014.02); *A61M 16/0638* (2014.02); *A61M 16/0825* (2014.02); *A62B 18/02* (2013.01); *A62B 18/08* (2013.01); *B29C 45/16* (2013.01); *B32B 7/02* (2013.01); *A61M 16/101* (2014.02); *Y10T 428/1352* (2015.01); *Y10T 428/1379* (2015.01); *Y10T 428/1386* (2015.01); *Y10T 428/24008* (2015.01); *Y10T 428/24612* (2015.01); *Y10T 428/24628* (2015.01); *Y10T 428/24752* (2015.01); *Y10T 428/24777* (2015.01); *Y10T 428/24942* (2015.01); *Y10T 428/24983* (2015.01); *Y10T 428/24992* (2015.01)

(58) Field of Classification Search
CPC .............. A61M 16/06; A61M 16/0465; A61M 16/047; A61M 16/0605; A61M 16/0616; A61M 16/0622; A61M 16/0627; A61M 16/0633; A61M 16/0638; Y10T 428/1352; B29C 45/16; A62B 18/00; A62B 18/02; A62B 18/08; F16L 11/00; F16L 11/02; F16L 11/04; F16L 11/08; F16L 11/081; F16L 11/082; F16L 11/083; F16L 11/085; F16L 11/086; F16L 11/087; F16L 11/088; F16L 11/10; F16L 11/24
See application file for complete search history.

(56) References Cited

U.S. PATENT DOCUMENTS

| | | | | |
|---|---|---|---|---|
| 4,413,359 | A * | 11/1983 | Akiyama | .................. A61F 2/00 |
| | | | | 128/899 |
| 4,848,334 | A * | 7/1989 | Bellm | ................... A61M 16/06 |
| | | | | 128/206.24 |
| 4,942,873 | A | 7/1990 | Irwin et al. | |

(Continued)

*Primary Examiner* — Walter Aughenbaugh
(74) *Attorney, Agent, or Firm* — Abel Schillinger, LLP

(57) ABSTRACT

A medical/technical device comprised of at least two materials. The materials are connected at least partially to each other permanently by a manufacturing process.

40 Claims, 8 Drawing Sheets

(51) Int. Cl.
*B32B 7/02* (2019.01)
*A61M 16/10* (2006.01)

(56) References Cited

U.S. PATENT DOCUMENTS

| | | | | |
|---|---|---|---|---|
| 5,573,039 A * | 11/1996 | Mang | ............... | F16L 11/12 |
| | | | | 138/137 |
| 5,647,357 A * | 7/1997 | Barnett | ............... | A61M 16/06 |
| | | | | 128/205.25 |
| 6,946,092 B1 | 9/2005 | Bertolino et al. | | |
| 7,971,590 B2 * | 7/2011 | Frater | ............... | A61M 16/06 |
| | | | | 128/206.21 |
| 8,535,771 B2 * | 9/2013 | Eifler | ............... | A61M 16/0638 |
| | | | | 128/205.25 |
| 8,684,004 B2 * | 4/2014 | Eifler | ............... | A61M 16/06 |
| | | | | 128/200.24 |
| 8,887,726 B2 * | 11/2014 | Schulz | ............... | A61M 16/06 |
| | | | | 128/205.25 |
| 2007/0267012 A1 * | 11/2007 | McCarthy | ............... | B29C 45/0013 |
| | | | | 128/201.11 |

* cited by examiner

DEVICE CONSISTING OF AT LEAST TWO MATERIALS

CROSS-REFERENCE TO RELATED APPLICATIONS

The present application is a continuation of U.S. patent application Ser. No. 12/317,259, filed Dec. 19, 2008, the entire disclosure of which is expressly incorporated by reference herein, which claims priority under 35 U.S.C. of German patent application 10 2007 062 445.1, filed Dec. 20, 2007.

BACKGROUND OF THE INVENTION

1. Field of the Invention

The present invention relates to medical functional elements, particularly in breathing masks, CPAP devices, breathing devices, hoses, sensors, moisturizers, and other medical/technical devices which are in contact with patients, wherein the new devices are configured to be easily cleanable.

2. Description of the Related Art

In order to connect two different materials, for example, for connecting a mask base body of hard plastic material with a soft mask bead of a soft elastomer, the so called two-component injection molding process is used. In this process, the hard component is configured in such a way that it can be manufactured by injection molding in a first manufacturing step. Subsequently, this component is placed into another mold, wherein the other mold still has hollow spaces when the component is placed therein. These hollow spaces are filled in a second step with a second material which in most cases is different from the first material. These components are then usually inseparably connected to each other by chemical, physical, or positively engaging connecting mechanisms.

An example of this two-component process is the use in medical breathing masks which are composed of a solid mask base body which provides in the mask the necessary stability and strength, and a mask bead which provides the sealing surface between mask and patient.

In a first step, the mask base body, usually of polycarbonate, polypropylene or polyamide (PC, PP, PA) is manufactured, and, in a second step, the mask bead, usually of silicon or thermoplastic elastomers (TPE) is injection molded onto the base body.

In plastics technology, as well as in other injection molding processes, it is attempted to dimension the wall thicknesses of a part to be injection molded uniformly. This prevents the formation of bubbles and sinks during the later cooling process. These bubbles and sinks become apparent in a transparent portion through the formation of bubbles in the material or by recessed surfaces in any type of material.

It is also known that an injection molded part can have a significantly better stability when it is provided with ribs.

In many medical/technical applications, moving and movable parts are necessary for carrying out certain functions. To be mentioned in this connection and examples may be locking elements, snap-in elements or other functional elements which, after being deflected, return automatically back into the original position if they are not prevented by a counterforce.

It is also known in the art that rigid materials are required for facilitating locking elements and snap-in elements. Rigid materials are brittle and, therefore, are very susceptible to breakage. This susceptibility to breakage is prevented if longer lever arms are constructed of the hard or brittle materials in order to distribute the forces over a large area when the elements are deflected.

In many cases, resilient elements are made of plastics materials which have a small thickness and are of oblong configuration.

In the attempt to prevent in injection molded parts with different wall thicknesses or transitions which are not smooth between two different wall thicknesses and to thereby prevent the formation of bubbles and sinks, frequently the surfaces of such a component are provided with a significant number of ribs and the resulting small radii, or are provided with corners and edges.

These dirt traps are very difficult to keep clean, particularly if patients have to frequently clean the medical articles, for examples masks, which are hygienic articles. In these systems which have been used in the past cleaning is possible only to a limited extent.

This effect is further increased by the formation of ribs at the actual casing. These dirt traps also occur if very fine locking elements, nap-in elements or other movable parts are present as functional elements in a device.

For example, lever arms are provided in closures which when one closure partner is inserted into the other closure partner, lever arms are provided which are deflected by a guide means provided at the other closure partner, until they are no longer guided and can once again snap back into their original position. The movement areas which are required for the deflection of the closure partners, do not have material and are usually constructed so has to be small and with fine surfaces, so that there are susceptible to dirt and are difficult to clean.

In order to be able to carry out the resilient effect, the resilient elements of plastic material require free movement space which is also very difficult to clean.

SUMMARY OF THE INVENTION

It is the primary object of the present invention to configure a device of the above-described type in such a way that it has a reduced tendency to become dirty and is easier to clean.

The present invention provides a medical/technical device which consists of at least two materials. These materials are permanently connected to each other in a manufacturing process. The process may be carried out as an injection molding process in which in one tool is mounted, for example, a mold half so as to be rotatable or otherwise pivotable, so that a first component is manufactured in a first manufacturing step. This first component is placed after it is manufactured continuously on the rotatable mold plate and is positioned in another cavity for the second manufacturing step. This cavity receives the complete first component and additionally provides hollow spaces between the first component and the second mold. The hollow spaces are then filled out with a second material in a second manufacturing step. In accordance with the invention, the first component is of a material which is harder than the material of the second component. It is also conceivable to first manufacture the second component and then to join the hard component with this soft component.

In some machines these manufacturing processes can be carried out in a single step; in other cases, these steps are carried out in two different machines.

It is particularly emphasized that the concept of the present invention of injection molding a second material onto the first material small radii are prevented which could lead to inadequate cleaning of the devices.

The two materials flow into each other spatially in a shadow projection. The first material has at a first location after the first manufacturing process a radius A and the second material has after the second manufacturing process a radius B at the same location and/or in the area of the first location.

In accordance with the present invention, the surfaces of both materials may be adapted to each other tangentially or the outer surfaces of the materials transition into each other. Moreover, it is being considered to permit the transition to have a maximum offset caused by the manufacture of the two materials relative to each other of about 0.5 mm, preferably about 0.3 mm.

In a particularly preferred embodiment of the invention, a radius B is created which is greater than the radius A of the other material. In an embodiment of the invention, the two materials are the same or are similar with respect to material or material characteristics. In another embodiment of the invention, the materials may differ with respect to structural and/or material characteristics.

In accordance with a particularly preferred embodiment, the two materials have a different hardness. In a further embodiment of the invention, the first material may be selected only for reasons of stability, so that the second material determines the outer shape and is at least partially arranged around the first material. In accordance with the invention, the materials are connected to each other chemically or through positive engagement or frictional engagement, or by material engagement or by adhesive surfaces.

In accordance with a particularly preferred embodiment, the locations of the second material within a space in a medical respiratory component are arranged in a targeted manner in such a way that a second material reduces the dead space of the medical/technical component. In most cases, the medical component is a breathing mask or an endotracheal tube (patient interface).

In another embodiment it is being considered to construct the air-conducting internal space of a patient interface PI or an accessory part of a medical device for supplying breathing gas in such a way that the second material influences the flow of the gas circulating in the medical/technical device.

In another particularly preferred embodiment of the invention, the free spaces of the first material are filled out with the second material. This may be carried out completely or partially, so that these dirt traps are also eliminated.

In many cases, these spaces can constitute movement spaces in order to make it possible for the functional elements to be deflected at least temporarily into these free spaces for effecting the function. In most cases, the functional element may be composed of the first material and may be filled by the second material.

In order to continue to ensure the function of the functional element of the first material it is being considered to fill out the free spaces with a compressible and/or elastic material. In a first state, the second material can be unloaded, i.e., no external forces act on the second material. If the functional element is actuated, it is deflected and torsion, expansion and/or upsetting of the second material which is connected to the first material takes place.

If the second material is a material which automatically returns into its original shape, the restoring forces within the material, together with the restoring forces of the first material if this first material does have such restoring forces, lead to the formation of a counterforce which acts opposite the original direction of deflection.

In other words, movable, functional elements may be formed of the first material which, when the second material is moved, is deformed in such a way that the restoring forces of the second material contribute at least partially to the restoration of the functional element.

In accordance with another embodiment of the invention, a functional element manufactured from the first material may be supported or held by an element or functional element made of the second material.

In accordance with another embodiment of the invention, the first material may be hard and may serve for arranging two adjacent surfaces in such a way that these surfaces assume the function of a locking element and/or snap-in element and/or support member.

Since the function of a movement and possibly a resilient effect or a restoring effect in small and fine elements is not existing, the function of a movement through an element of the second material can be carried out.

Considered as the preferred materials are elastomers for the second material (for example, silicon, TPE) and materials such as PP, ABS, PA, or PC for the first material. Also conceivable are silicons of different hardnesses.

In a particularly preferred embodiment of the invention, the medical/technical device forms a mask base body and at least one element which remains in its position. In accordance with the invention, this element has two states. The first state is the adjustment state in which the position relative to the mask base body is adjusted. The second state is the state of utilization. In accordance with the invention, it is being considered that the force required for adjustment is greater than the force acting at least in one state of use on the element to be adjusted. The patient adjusts the desired position of use and must apply a certain force to achieve the position. After the adjustment the patient utilizes the mask which, because of the smaller forces acting on the mask and the adjusting element thereof, cannot be adjusted as a result of the use because of the small forces which act on the mask and the adjusting element. The advantage is a simple and secure adjustment and readjustment of mask elements in which, for example, no additional elements have to be actuated.

In accordance with another embodiment of the invention, the adjustment can be without steps or with steps. In accordance with a particularly preferred embodiment of the invention, the force required for the adjustment to overcome a locking action or a frictional resistance. In accordance with another embodiment, the frictional resistance can act through at least one element on the adjustable element.

Consequently, the advantages provided by the invention are the provision of smooth transitions which can be easily cleaned and filling of the movement spaces with elastomer materials as the filling materials; another advantage is the filling of edges, ribs or other design elements which are required for stability and which also are produced as a result of the principle of uniform wall thicknesses and the support of very fine hard elements by elements of elastic materials.

A structural element according to the present invention may be used in any conceivable medical/technical device or an accessory or as a replacement part of a medical/technical device or in a medical article of use, wherein the following list of application areas is not conclusive or final. Fields of use are particularly in the area of a patient interface; a mask, a spherical joint, a spherical joint receiving element, a connection piece, an exhaling system, a tape system, a tape clip, a mask base body, a mask bead, a forehead padding, a forehead support, a nasal pillow or other breathing/technological components, such as a moisturizer, a connecting piece to a hose connection, a hose, a housing part of a breathing device, a sound damping box of a breathing device, an oxygen concentrator, a suction pump, a pulse oximeter, a sensor for a pulse oximeter or a sensor.

As a result of the use according to the invention of multi-component injection molding and an in-mold assembly, the present invention makes it possible to avoid complicated assembly steps. The plastic products consist of at least two individual components which are movable relative to each other but are permanently connected to each other. All components can be manufactured in a tool with an injection molding machine in one cycle/work step.

In accordance with another embodiment, it is intended to initially manufacture the soft components, for example, of silicon, in a mold using the injection molding process and subsequently to leave the finished soft component in the same mold in order to subsequently injection mold a hard component, for example, acyrlinitril-butadine-styrene (ABS), in a second manufacturing step and to permanently connect the soft and the hard components with each other. Preferably, injection molding of the second component is carried out at a point in time at which the first component is still heated by the injection molding process.

In accordance with an embodiment, the manufacture is carried out in such a way that in a mold initially the hard component is manufactured in an injection molding process and is left in the mold and, subsequently, a first soft component is injection molded at a first location to the hard component and, simultaneously or subsequently, a second soft component is injection molded at a second location to the hard component. Subsequently, the finished structural component is removed from the tool.

In accordance with the invention, in the area of an interface of a patient the contact area of two functional structural components, for example, hose connections, spherical joints, spherical joint receiving elements, exhaling systems, tape systems, tape clips, mask base bodies, mask beads, forehead cushions, forehead supports, and adjusting mechanisms for the forehead supports are manufactured in two-component technology. For example, transitions from hard PI bodies to hard hose connections are effected by means of a soft sealing lip which is injection molded onto the body by the two-component method. This provides the advantage that the soft sealing lip helps to prevent any possible leakages which may occur in the area of two art structural components. When the house connection is constructed as a spherical joint, it is intended to manufacture the joint area of the spherical receiving element in a two-component process, when the surface in this instance serves as a sliding surface for the bowl and is of hard material.

The contact area between hard and soft materials is of minimal dimensions in one embodiment, preferably having a layer thickness of below 2 mm, especially preferred below 1.5 mm and especially preferred with a layer thickness of 1.2 mm to 0.8 mm. In this connection, the contact area is preferably located at an end phase continuously over a length of at least 10 mm preferably over a length of at least 20 mm. This provides the advantage of a large contact area and a low cross-section. For example, the contact area between the hard mask body and the soft mask bead are constructed with a layer thickness of below 2 mm, especially preferred below 1.5 mm and especially preferred with a layer thickness of 1.2 mm to 0.8 mm continuously over a length of at least 10 mm preferably over a length of at least 20 mm.

In accordance with the invention, a single-piece patient interface composed of a hard body frame element and soft sealing element is manufactured in a two-component process, wherein the frame also has connection points for a tape system made of hard material, and an insertion opening for a hose connection is made available.

The various features of novelty which characterize the invention are pointed out with particularity in the claims annexed to and forming a part of the disclosure. For a better understanding of the invention, its operating advantages, specific objects attained by its use, reference should be had to the drawing and descriptive matter in which there are illustrated and described preferred embodiments of the invention.

DETAILED DESCRIPTION OF THE INVENTION

Figure 1:
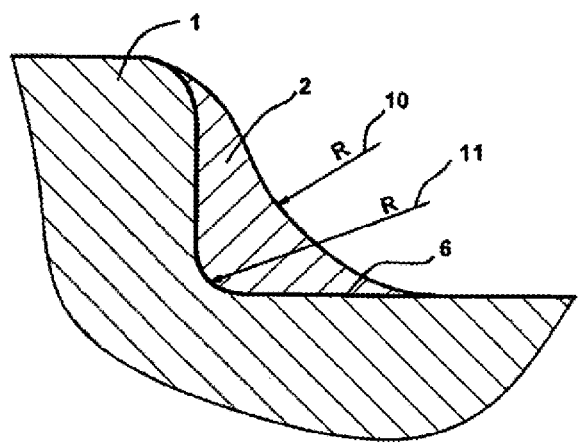
FIG. 1 is a sectional view of a material having two radii.

As illustrated in the drawing, FIG. 1 shows a portion of a shaped first part of a first material 1 which has a first radius. Injection molded onto this first part is a second material, so that the radius is increased by an integral or other connection. This facilitates the cleanability of the portion and lowers the susceptibility to dirt of this portion. In this case, the first material 1 is of a hard material and the second material 2 is a soft material which facilitates more pleasant wearing comfort to the patient and also facilitates an easier cleaning.

Figure 2:
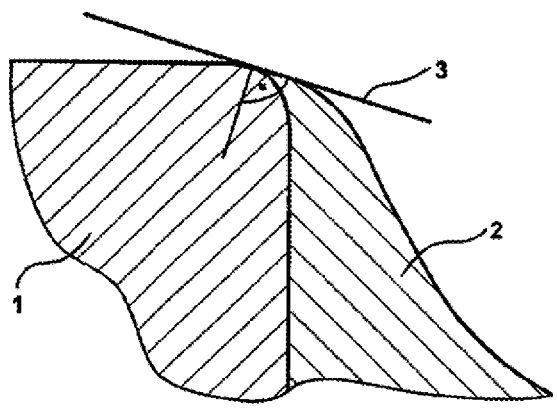
FIG. 2 is a sectional view showing the tangential adjustment of two materials to each other.

FIG. 2 shows the tangential mutual adjustment of a first material 1 and a second material 2, so that the transitions and run outs of one of the two materials are adjusted to each other by tangent 3. This embodiment achieves softer material transitions and serves to prevent sharp edges and corners or undercuts which are difficult to clean.

Figure 3:
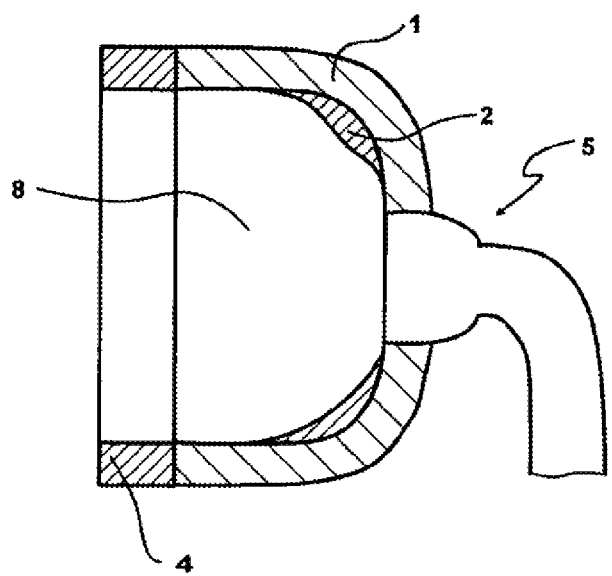
FIG. 3 is a sectional view showing the reduction of dead space by a second material.

FIG. 3 shows that arranged in a mask arrangement 5 with a mask body of a first material 1 and within the mask body are inserted elements within the mask body of a second material 2 which reduce the dead space and/or influence the flow pattern of the arrangement. Placed on the mask body may be a mask bead of a third material 4 or may be injection molded onto the mask body or otherwise be connected thereto.

Figure 4A:
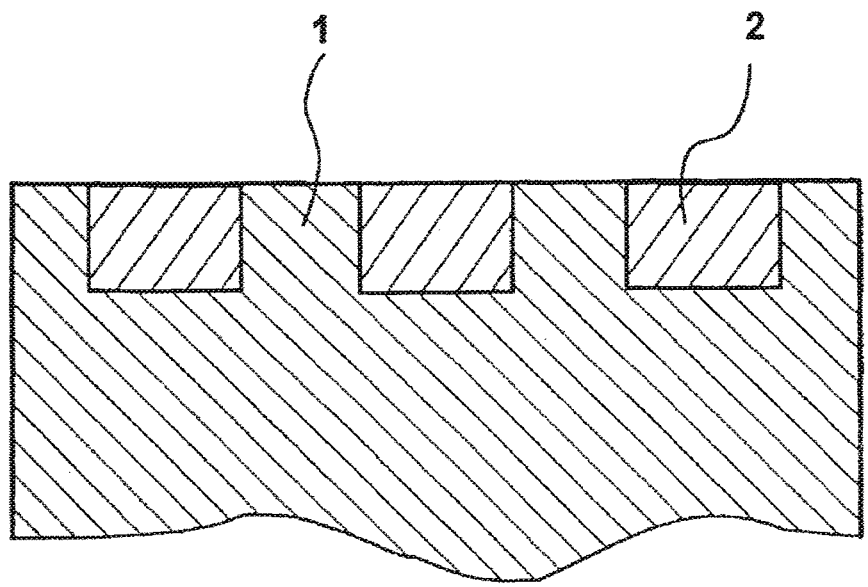
FIG. 4A is a sectional view showing filling out of movement spaces with a second material.

FIG. 4A shows a flush connection between two materials. In this case, the first material 1 is the principal component and the second material 2 serves for filling the 3 spaces of the first material. Because of different functions and material differences, the spaces filled out with the second material can serve as movement spaces of the projections from the first material 1.

Figure 4B:
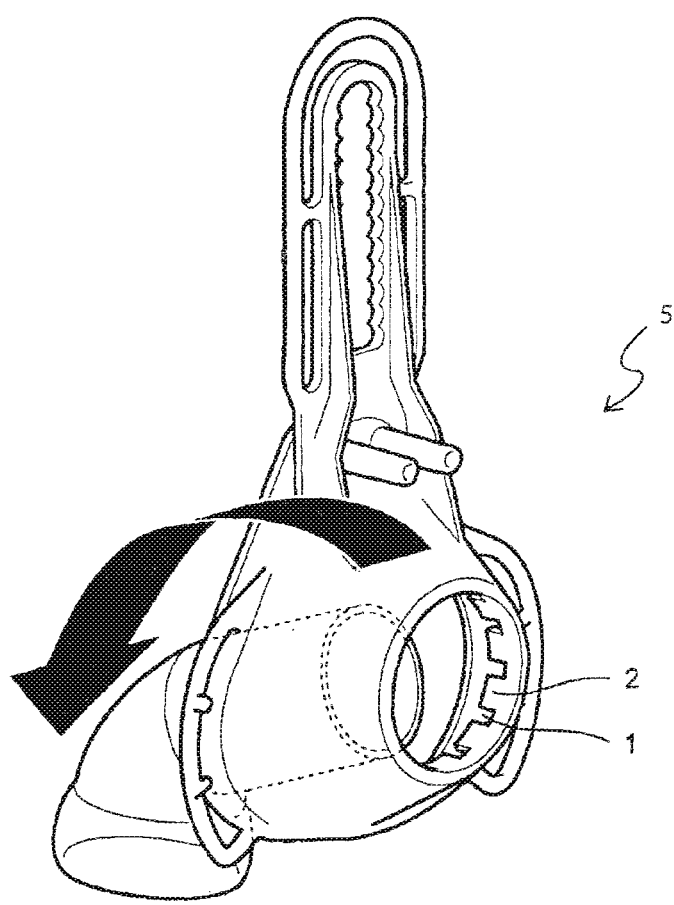
FIG. 4B shows an embodiment of an assembly of a connecting component.

FIG. 4B shows the assembly of a connecting component, in this embodiment a spherical joint, which is constructed as a hose adaptor at the mask body. The spherical joint is positioned together with the connecting piece for the hose in the region of the opening of the mask body provided for this purpose. Because of the arrangement of ribs in the area of the insertion opening and the size of the spherical joint corresponding to the ribs, the spherical joint can only be inserted by applying a defining force. As a result, coding is available.

When the body is inserted, the ribs are slightly bent, and the recesses filled with soft silicon material between the ribs are expanded to such an extent that the spherical joint can be passed through. The inserting connecting component is locked by means of restoring forces of the hard ribs, and by the restoring forces of the soft material. Basically, a reverse configuration is conceivable. An elastic locking of the locking element is reinforced by the fact that the ribs are also of a relatively soft material, so that the hard connecting component can be inserted into the recess of a mask body and can also be unscrewed therefrom again.

After the assembly process has concluded, the connecting component itself is held in position by clamping action of the ribs. The ribs engage around the connecting component, so that the total configuration also withstands tensile forces.

Figure 4C:
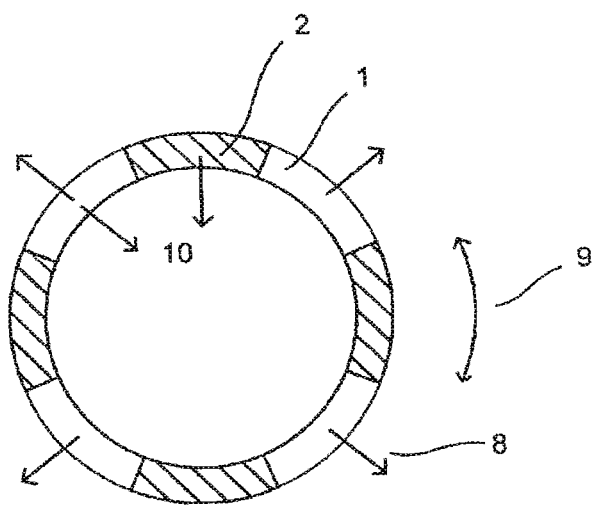
FIG. 4C shows a sectional view of a part of the assembly shown in FIG. 4B with gaps in a hard material being filled out with a soft material.

FIG. 4C shows gaps being filled out with soft material. Gaps in the hard material 1 are filled out with soft material. Gaps in the hard material 1 are filled out with the soft and elastic material 2. The desire flexibility of the part remains while no bacteria and no dirt can collect in the gaps.

Figure 5:
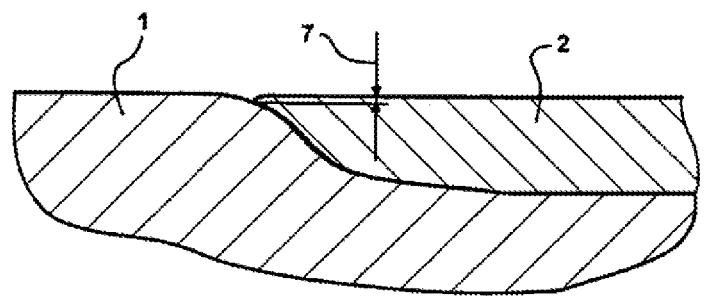
FIG. 5 is a sectional view showing the offset between two different materials.

FIG. 5 shows the offset 7 between the adjusted first material and the second material 2 which occurs in occurrences during the processing and manufacture.

Figure 6:
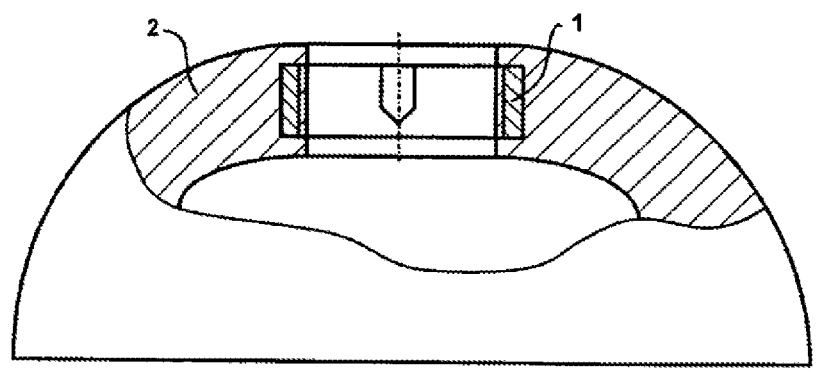
FIG. 6 is a sectional view embedding and support of very fine component of a second material.

FIG. 6 shows one element of a first material embedded in an element of a second material at least partially. As a result very fine parts of the first material 1 is supported and still maintains the required freedom of movement demonstrated as an example in a soft second material 2.

Figure 7:
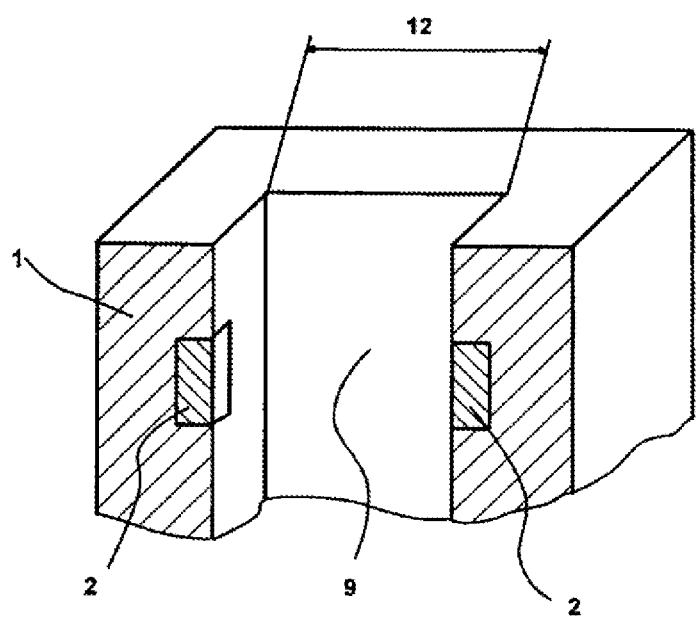
FIG. 7 is a prospective view of two oppositely located plates embedded in a second material.

FIG. 7 shows how an element of a first material 1 is supported by an element of a second material 2. If a suitable element of a similarly hard material as the second material 2 is inserted into the free space 9 and this element has a greater dimension than the width 12 of the first element 1, the two plates act as press plates against the element to be inserted and exert lateral forces against the element to be inserted. When the materials and the surface structures are correctly selected, the lateral force may act as friction partners.

Figure 8:
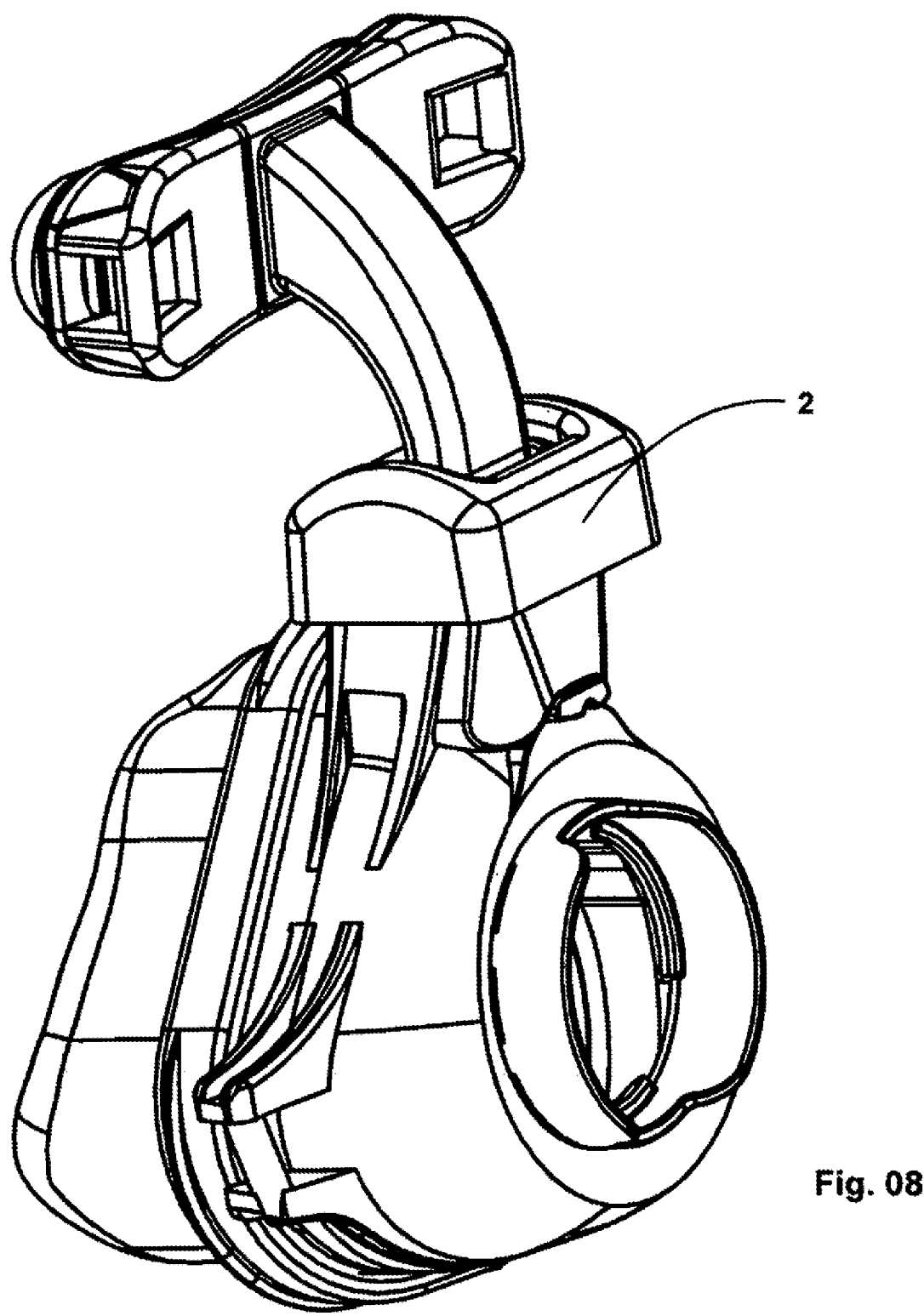
FIGS. 8 to 11 are perspective views showing various applications in the area of a forehead support made of different materials.

FIG. 8 is a perspective illustration of a patient interface constructed as a breathing mask with a forehead support in which a transition are of a column of the forehead support is covered by a cap-like second material 2.

Figure 9:
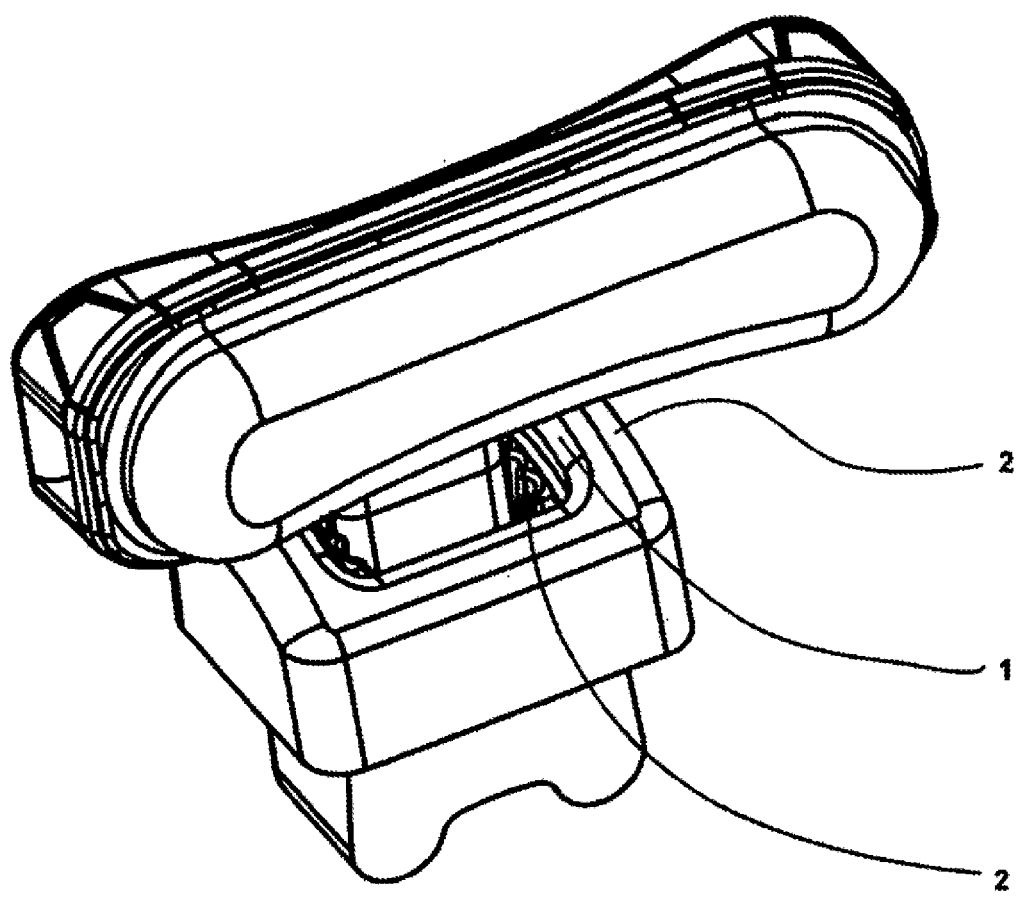

FIG. 9 shows a perspective partial top view of the arrangement of FIG. 8. In this case, a different material 1 is embedded between two materials 2. This material 1 is elastic and compressible and thereby facilitates a movement of the forehead support in the receiving element of the mask body.

When the desired locking position is reached, the restoring forces of the material 1 and the end support result in a stable locking position in the receiving element. Consequently, a locking connection is realized which is safely and easily operated.

Figure 10:
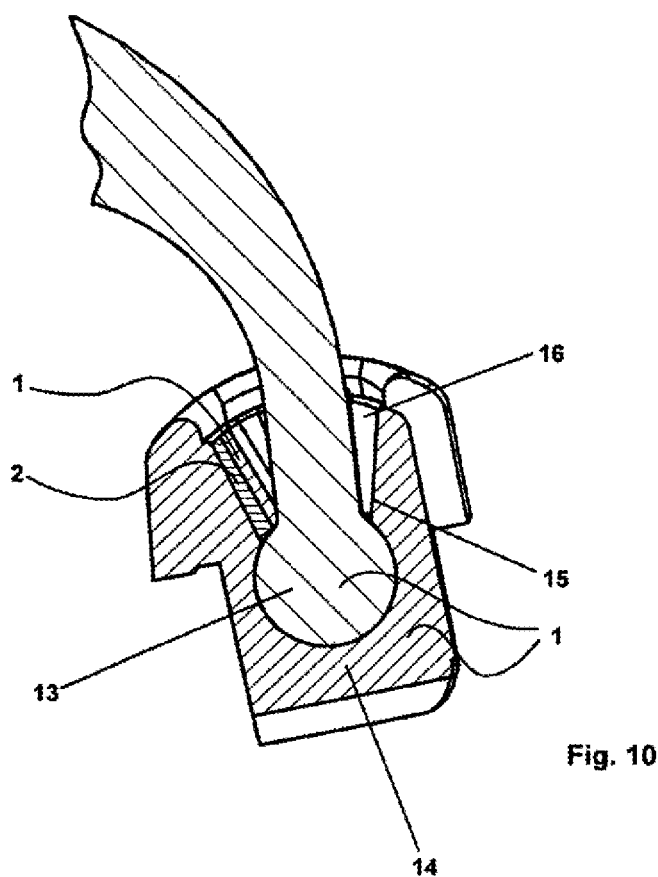

FIG. 10 shows in a sectional view the support of the column of the forehead support in a corresponding counter bearing which is held by the breathing mask. The end element of the forehead support 13 is constructed cylindrically and complementary to the receiving element in the counter bearing 14 of the mask body. The counter bearing and the end element of the forehead support are each manufactured of a hard material 1. The inner surface of the counter bearing is also made of a hard material 1. In the area of the insertion opening 16 up to the securing element 15, i.e., a reduced diameter portion, a soft compressible material 2 is located underneath the surface thereof.

This facilitates an easy insertion of the end element of the forehead support in the receiving element in the counter bearing 14 of the mask body. In addition, a high stability of the jointly connection is achieved in the state of the operation as well as in the state of rest in the selected locking position.

The insertion opening 16 of the counter bearing is dimensioned in such a way that the end element of the forehead support can be easily inserted. A reduced diameter portion is located approximately in the middle of the maximum possible insertion depth, wherein the reduced diameter portion serves as a securing element 15 and prevents an unintentional slippage of the end element of the forehead support out of the counter bearing. The reduced diameter portion is dimensioned in such a way that the end element of the forehead support cannot pass the area of the reduced diameter portion without the application of a force.

In the area of the securing element, the end element of the forehead support is dimensioned somewhat greater than that of the reduced diameter portion. The end element of the forehead support can pass this area only by the application of a force. The inner surface of the counter bearing, in this case, the sliding surface, is pressed against the soft compressible material which is located underneath and which is so compressed as a result of the force application that the securing element is pressed away and the end element of the forehead support can just be passed. Subsequently, the soft compressible material 2 once again expands, so that the end element of the forehead support is held in the counter bearing. The movement of the forehead support illustrated in this application is a pivoting movement. According to the invention, it is also possible to utilize a linear adjustment of the forehead support by using the above-described combination of hard and soft materials. According to the invention, a patient interface, such as a mask for breathing, a nasal pillow or a sensor for collecting patient data, has a base body and at least 1 element whose position is adjustable. Because of the combination of soft and hard materials, the force required for the adjustment is greater than the force which acts in at least one state of use on the element to be adjusted.

Figure 11:
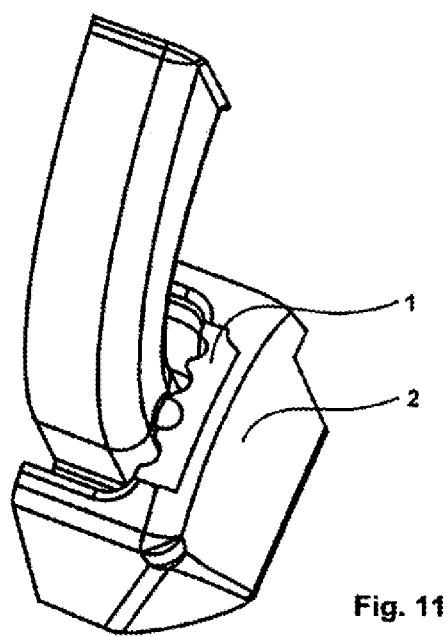

FIG. 11 shows another pairing of a first material 1 and a second material 2 in the area of the support of the column of a forehead support.

Figure 12:
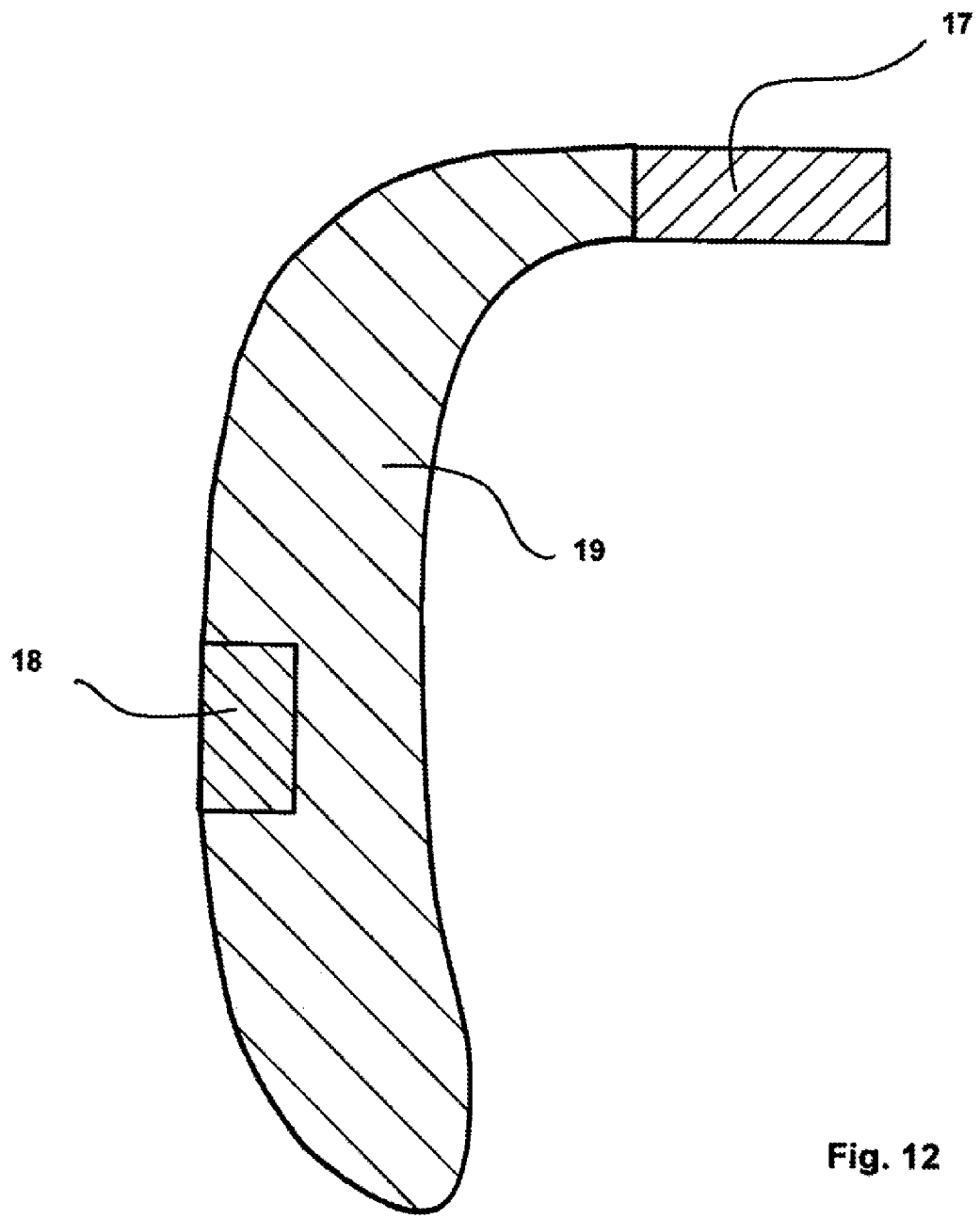
FIG. 12 shows two components of one or differently hard materials connected with a soft material.

FIG. 12 shows the combination of three different materials, wherein these materials preferably have different hardness and are permanently connected to each other. In this sectional view, a hard central element 17 of a mask body is located at the top and the hard frame 18 of the mask is on the left. The injection molded silicon body with the bead contour is made of a soft material 19. Due to the manufacturing process, hard and soft components are permanently and rigidly connected to each other.

It is also provided in accordance with the present invention that a great portion of the material is the soft material with embedded hard materials, wherein the hard components also serve a supporting function.

In accordance with another embodiment of the invention, functional elements which, for example, cause the adjustment of a forehead support are made of a hard material and the functional elements are surrounded by a soft material, in particular by silicon. Due to the expandability of silicon, the mobility continues to be possible without limitations. However, the contact points of the functional elements are protected against contamination.

Another advantage of the invention is the fact that the number of parts is reduced. This aspect is realized, for example, by instructing a closure of a pressure measuring pipe of a patient interface PI as a component of the soft sealing section. It is also conceivable to construct the pressure measuring pipe as a component of the soft sealing portion. The manufacture takes place by means of the injection molding process of the same material, for example, of silicon. The pressure measuring pipe is part a body made of a hard material, a PI. Both components of the PI and the sealing section are connected to each other by the two-component method. Consequently, a single patient interface is created.

While specific embodiments of the invention have been shown and described in detail to illustrate the inventive principles, it will be understood that the invention may be embodied otherwise without departing from such principles.

What is claimed is:

1. A medical/technical device comprised of at least a first material and a second material which is different from the first material, wherein the medical/technical device is a patient interface in the form of a mask or is at least one of a spherical joint, a spherical joint receiving element, an exhaling system, a tape system, a tape clip, a forehead padding, a forehead support, a nasal pillow, a moisturizer, a connecting piece to a hose connection, a housing part of a breathing device, a sound damping box of a breathing device, an oxygen concentrator, a suction pump, a pulse oximeter or a sensor for a pulse oximeter, wherein the first and second materials are at least in part connected to each other permanently and one or more free spaces present in the first material are filled at least partially with the second material, and wherein at least one of
   (i) the second material has a higher hardness than the first material,
   (ii) more than one free space is present in the first material and filled at least partially with the second material,
   (iii) the one or more free spaces comprise spaces formed by adjacent ribs of the first material,
   (iv) the second material is embedded at least partially in the first material.

2. The device of claim 1, wherein the medical/technical device is at least one of a spherical joint, a spherical joint receiving element, an exhaling system, a tape system, a tape clip, a forehead padding, a forehead support, a nasal pillow, a moisturizer, a connecting piece to a hose connection, a housing part of a breathing device, a sound damping box of a breathing device, an oxygen concentrator, a suction pump, a pulse oximeter or a sensor for a pulse oximeter.

3. The device of claim 1, wherein the second material has a higher hardness than the first material.

4. The device of claim 2, wherein the second material has a higher hardness than the first material.

5. The device of claim 1, wherein more than one free space is present in the first material and filled at least partially with the second material.

6. The device of claim 2, wherein more than one free space is present in the first material and filled at least partially with the second material.

7. The device of claim 2, wherein the second material comprises ABS, PP, PC or PA.

8. The device of claim 2, wherein the first material comprises a silicone or a thermoplastic elastomer.

9. The device of claim 1, wherein the one or more free spaces comprise spaces formed by adjacent ribs of the first material.

10. The device of claim 2, wherein the one or more free spaces comprise spaces formed by adjacent ribs of the first material.

11. The device of claim 2, wherein the second material is embedded at least partially in the first material.

12. The device of claim 11, wherein the second material has a higher hardness than the first material.

13. The device of claim 1, wherein the first and second materials are at least in part permanently connected to each other chemically.

14. The device of claim 1, wherein the first and second materials are at least in part permanently connected to each other by gluing, welding, or riveting.

15. The device of claim 1, wherein the first and second materials are at least in part permanently connected to each other by injection molding.

16. The device of claim 2, wherein one of the first and second materials is a softer material, which softer material is at least partially a sealing element.

17. The device of claim 1, wherein the first and second materials are connected to each other by a third material.

18. The device of claim 2, wherein the first and second materials are connected to each other by a third material.

19. The device of claim 2, wherein the first and second materials comprise silicones of different hardness.

20. The device of claim 2, wherein the first material serves to arrange two adjacent surfaces in such a way that these surfaces assume a function of a locking element and/or snap-in element and/or support member.

21. The device of claim 2, wherein the second material can be unloaded in a first state and compressed and/or expanded and/or torsioned in another state, a restoring force being directed to the first material.

22. A process for manufacturing the medical/technical device of claim 1, wherein the process comprises at least in part connecting the first and second materials to each other permanently by injection molding such that one or more free spaces present in the first material are filled at least partially with the second material.

23. The process of claim 22 wherein the injection molding comprises multi-component injection molding.

24. A process for manufacturing a medical/technical device, wherein the device is comprised of at least a first material and a second material which is different from the first material, the first and second materials comprising silicones of different hardness and being at least in part connected to each other permanently, and a concave surface formed by the first material and having a first radius of curvature being at least partially covered by the second material to form a concave surface having a second radius of curvature which is larger than the first radius of curvature, and wherein the method comprises at least in part connecting the first and second materials to each other permanently by injection molding such that a concave surface formed by the first material and having a first radius of curvature is at least partially covered by the second material to form a concave surface having a second radius of curvature which is larger than the first radius of curvature.

25. The process of claim 24 wherein the injection molding comprises multi-component injection molding.

26. A medical/technical device comprised of at least a first material and a second material which is different from the first material, wherein the medical/technical device is at least one of a spherical joint, a spherical joint receiving element, an exhaling system, a tape system, a tape clip, a forehead padding, a forehead support, a nasal pillow, a moisturizer, a connecting piece to a hose connection, a housing part of a breathing device, a sound damping box of a breathing device, an oxygen concentrator, a suction pump, a pulse oximeter or a sensor for a pulse oximeter and wherein the first and second materials are at least in part connected to each other permanently and a concave surface formed by the first material and having a first radius of curvature is at least partially covered by the second material to form a concave surface having a second radius of curvature which is larger than the first radius of curvature.

27. The device of claim 26, wherein the first and second materials differ in a hardness thereof.

28. The device of claim 26, wherein the first and second materials are at least in part permanently connected to each other chemically.

29. The device of claim 26, wherein the first and second materials are at least in part permanently connected to each other by adhesive surfaces.

30. The device of claim 26, wherein the first and second materials are at least in part permanently connected to each other by gluing, welding, or riveting.

31. The device of claim 26, wherein the first and second materials are at least in part permanently connected to each other by injection molding.

32. The device of claim 26, wherein one of the first and second materials is a softer material, which softer material is at least partially a sealing element.

33. The device of claim 26, wherein the first and second materials are connected to each other by a third material.

34. The device of claim 26, wherein the first material comprises ABS, PP, PC or PA.

35. The device of claim 26, wherein the second material comprises a silicone or a thermoplastic elastomer.

36. The device of claim 34, wherein the second material comprises a silicone or a thermoplastic elastomer.

37. A process for manufacturing the medical/technical device of claim 26, wherein the process comprises at least in part connecting the first and second materials to each other permanently by injection molding such that a concave surface formed by the first material and having a first radius of curvature is at least partially covered by the second material to form a concave surface having a second radius of curvature which is larger than the first radius of curvature.

38. The process of claim 37, wherein the injection molding comprises multi-component injection molding.

39. The process of claim 37, wherein the first material comprises ABS, PP, PC or PA.

40. The process of claim 37, wherein the second material comprises a silicone or a thermoplastic elastomer.

* * * * *